(12) United States Patent
Yokoyama

(10) Patent No.: US 11,260,159 B2
(45) Date of Patent: Mar. 1, 2022

(54) PERCUTANEOUS CATHETER AND PERCUTANEOUS CATHETER ASSEMBLY

(71) Applicant: TERUMO KABUSHIKI KAISHA, Tokyo (JP)

(72) Inventor: Kenji Yokoyama, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 674 days.

(21) Appl. No.: 16/194,569

(22) Filed: Nov. 19, 2018

(65) Prior Publication Data

US 2019/0083695 A1    Mar. 21, 2019

Related U.S. Application Data

(63) Continuation of application No. PCT/JP2017/008828, filed on Mar. 6, 2017.

(30) Foreign Application Priority Data

Jun. 7, 2016 (JP) .............................. JP2016-113694

(51) Int. Cl.
    *A61M 1/36*       (2006.01)
    *A61M 25/00*      (2006.01)
    *A61M 25/01*      (2006.01)

(52) U.S. Cl.
    CPC ............ *A61M 1/3639* (2013.01); *A61M 1/36* (2013.01); *A61M 25/00* (2013.01);
    (Continued)

(58) Field of Classification Search
    CPC ....... A61L 29/14; A61M 1/36; A61M 1/3639; A61M 1/3659; A61M 1/3661;
    (Continued)

(56) References Cited

U.S. PATENT DOCUMENTS 5,295,994 A    3/1994 Bonutti
5,341,818 A    8/1994 Abrams
(Continued)

FOREIGN PATENT DOCUMENTS

CN    101938933 A    1/2011
JP    2014050549 A    3/2014
(Continued)

OTHER PUBLICATIONS

Japan Patent Office, International Search and Opinion Report, PCT/JP2017/008828, dated Jun. 6, 2017.
(Continued)

*Primary Examiner* — Benjamin J Klein
(74) *Attorney, Agent, or Firm* — MacMillan, Sobanski & Todd, LLC

(57) ABSTRACT

A percutaneous catheter provides an adjustable diameter in order to reduce pressure loss, maintain a required flow, and avoid increasing a load to the patient. A catheter tube is formed of braided wires in an intersecting manner and extends in an axial direction. A distal tip is affixed to a distal side of the catheter tube and is configured to engaged a distal end of a dilator. The catheter tube includes a non-coated portion on a proximal side of the distal tip and a coated portion embedded in a resin material. An inner diameter of the non-coated portion is larger than an outer diameter of the dilator. When the dilator is fully inserted through the percutaneous catheter, the non-coated portion expands in the axial direction, reducing its in inner diameter so that an inner surface of the non-coated portion comes into tight contact with an outer surface of the dilator.

9 Claims, 10 Drawing Sheets

(52) U.S. Cl.
CPC ........ *A61M 25/0023* (2013.01); *A61M 25/01* (2013.01); *A61M 25/007* (2013.01)

(58) Field of Classification Search
CPC .............. A61M 25/00; A61M 25/0023; A61M 25/0068; A61M 25/007; A61M 25/01; A61M 39/0247; A61M 2025/0024; A61M 2025/0025; A61M 2025/0031; A61M 2039/0258; A61M 2039/0266
See application file for complete search history.

(56) References Cited

U.S. PATENT DOCUMENTS

| | | | |
|---|---|---|---|
| 5,405,380 | A | 4/1995 | Gianotti et al. |
| 6,626,859 | B2 | 9/2003 | von Segesser |
| 6,673,042 | B1 | 1/2004 | Samson |
| 7,748,275 | B2 | 7/2010 | Kouda et al. |
| 8,398,587 | B2 | 3/2013 | Dewaele |
| 2002/0010440 | A1* | 1/2002 | Segesser ............ A61B 17/3439 604/272 |
| 2003/0120223 | A1 | 6/2003 | Von Segesser |
| 2011/0282156 | A1 | 11/2011 | Lenker |
| 2014/0058429 | A1 | 2/2014 | Tegels |

FOREIGN PATENT DOCUMENTS

| | | |
|---|---|---|
| WO | 2005-002454 A1 | 1/2005 |
| WO | 2005-046425 A2 | 5/2005 |

OTHER PUBLICATIONS

International Search and Opinion Report, PCT/JP2017/008828, dated Jun. 6, 2017.
Extended European Search Report and Opinion, EP17809900.8, dated Jan. 9, 2020.
Office Action of Chinese Patent Office, Chinese application 201780022062, dated Oct. 28, 2020.

* cited by examiner

US 11,260,159 B2

PERCUTANEOUS CATHETER AND PERCUTANEOUS CATHETER ASSEMBLY

CROSS REFERENCE TO RELATED APPLICATIONS

This application is a continuation of PCT Application No. PCT/JP2017/008828, filed Mar. 6, 2017, based on and claiming priority to Japanese Application No. 2016-113694, filed Jun. 7, 2016, both of which are incorporated herein by reference in their entirety.

BACKGROUND OF THE INVENTION

The present invention relates to a percutaneous catheter and a percutaneous catheter assembly.

In the related art, treatment has been performed by a percutaneous cardiopulmonary support (PCPS) method for performing cardiopulmonary resuscitation during emergency treatment, circulation support, and respiratory support. This percutaneous cardiopulmonary support method is a method of temporarily supporting and substituting a cardiopulmonary function using an extracorporeal circulator.

An extracorporeal circulator includes an extracorporeal circulation circuit constituted of a centrifugal pump, an artificial lung, a blood removing path, a blood feeding path, and the like. The extracorporeal circulator exchanges gas in removed blood and feeds the blood to the blood feeding path. In regard to that described above, for example, U.S. Pat. No. 7,748,275 discloses a circulation circuit of an extracorporeal circulator.

In a case where blood circulation is performed with this circulation circuit, blood circulates due to a force of a pump driven by a motor. Therefore, in order to suitably perform blood circulation, a pressure loss in a tube constituting the circulation circuit is required to be reduced.

However, if a tube has a small inner diameter, a pressure loss increases and a flow rate for flowing in the circulation circuit is reduced. Therefore, unless the size of the inner diameter of the tube is sufficiently large, a required circulation amount of blood cannot be obtained.

On the other hand, if the inner diameter of the tube is increased, the outer diameter of the tube is also increased. Therefore, if the inner diameter of a blood removing catheter (tube) or a blood feeding catheter (tube) inserted into the body of a patient is increased, the degree of an invasion to the body of the patient increases, so that a load to the body of the patient increases.

SUMMARY OF THE INVENTION

An object of the present invention is to provide a percutaneous catheter in which a load to the body of a patient can be minimized, a pressure loss of liquid circulating in a circulation circuit can be reduced, and a required flow rate of the liquid can be ensured; and a percutaneous catheter assembly with such improved catheter.

In order to achieve the object described above, there is provided a percutaneous catheter through which blood passes and which is expandable in an axial direction under control of a dilator inserted through the percutaneous catheter. The percutaneous catheter includes a catheter tube that extends in the axial direction, and a distal tip that is provided at a distal end of the catheter tube and is configured to allow the dilator to be attached to the distal tip. The catheter tube includes a non-coated portion which is provided on a proximal side of the distal tip and is formed of wires braided in an intersecting manner, and a coated portion which is provided on the proximal side of the non-coated portion and is formed by coating the wires braided in an intersecting manner with a resin material. An inner diameter of the non-coated portion is configured to be larger than an outer diameter of the dilator before the dilator is inserted through the percutaneous catheter. When the dilator is inserted through the percutaneous catheter, the non-coated portion expands in the axial direction and is reduced in inner diameter so that an inner peripheral portion of the non-coated portion comes into tight contact with an outer peripheral portion of the dilator.

In addition, in order to achieve the object described above, there is provided a percutaneous catheter assembly including the percutaneous catheter described above, and the dilator.

According to the percutaneous catheter and the percutaneous catheter assembly having configurations as described above, if the dilator is inserted through the percutaneous catheter by a distance sufficient to stretch the percutaneous catheter in the axial direction, the inner peripheral portion (i.e., cylindrical surface) of the non-coated portion comes into tight contact with the outer peripheral portion (i.e., cylindrical surface) of the dilator. Therefore, an outer diameter of the non-coated portion is reduced. It is possible to minimize a load to the body of a patient by inserting the percutaneous catheter into a living body while in this state. In addition, if the dilator is withdrawn from the percutaneous catheter after the percutaneous catheter indwells inside a living body, the catheter tube contracts in the axial direction and returns to the original state as the non-coated portion radially expands. At this time, since the inner diameter of the non-coated portion is larger than the outer diameter of the dilator, a pressure loss in the non-coated portion can be reduced and a required flow rate of liquid can be ensured.

DETAILED DESCRIPTION OF PREFERRED EMBODIMENTS

Hereinafter, with reference to the drawings, embodiments of the present invention will be described. The following description does not limit the technical scope or the meaning of the terms disclosed in Claims. In addition, for the convenience of description, there are cases where the dimensional ratios of the drawings are exaggerated and are different from the actual ratios.

Figure 1:
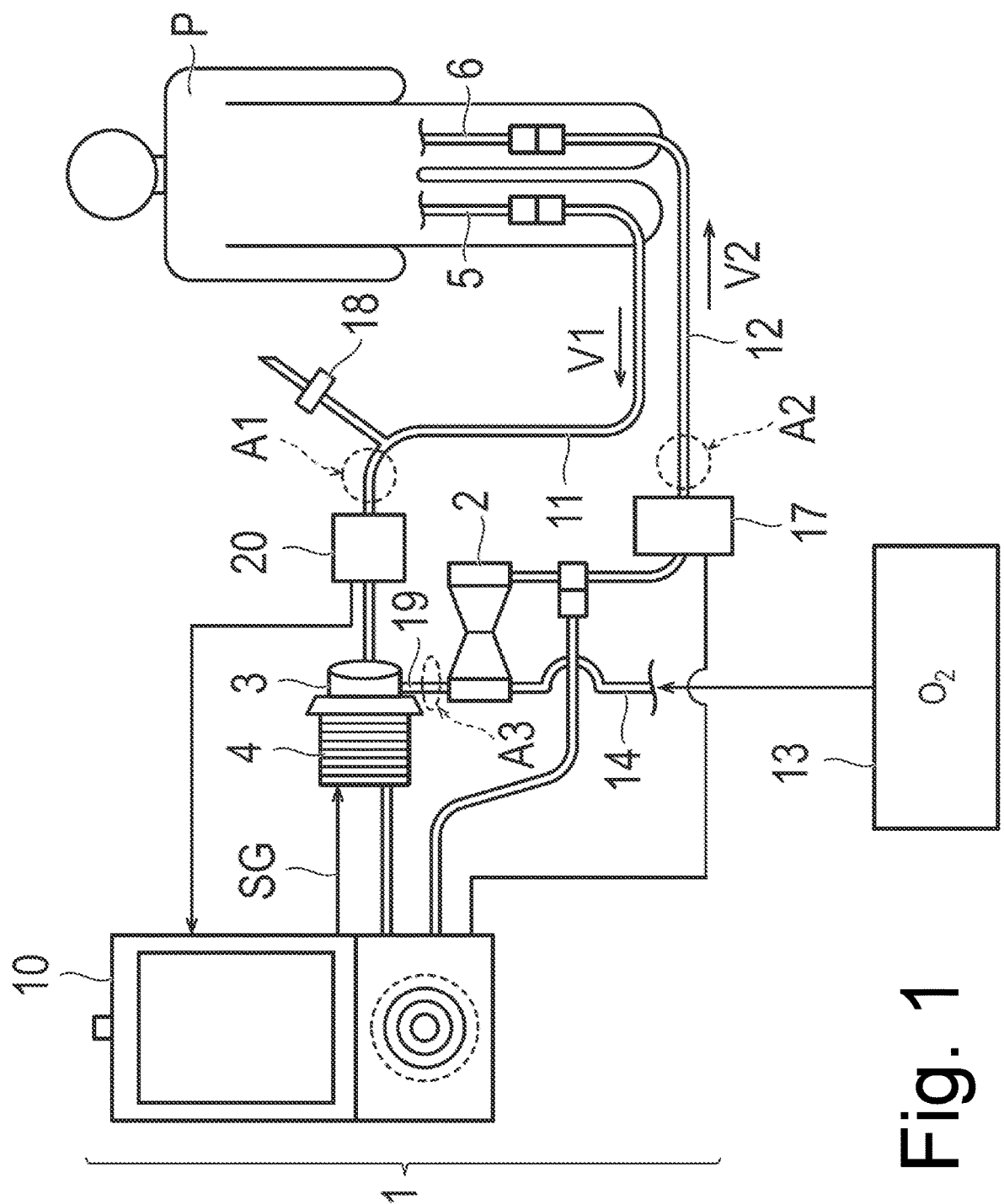
FIG. 1 is a system diagram illustrating an example of an extracorporeal circulator in which a percutaneous catheter according to an embodiment of the present invention is applied.

FIG. 1 is a system diagram illustrating an example of an extracorporeal circulator 1 in which a percutaneous catheter according to the embodiments of the present invention is applied and which is used in a percutaneous cardiopulmonary support (PCPS) method for temporarily supporting and substituting the functions of the heart and lungs until the cardiac function recovers when the heart of a patient is weak.

According to the extracorporeal circulator 1, a pump is operated to remove blood from the vein (vena cava) of a patient, and the blood is oxygenated by exchanging gas in the blood using an artificial lung 2. Thereafter, it is possible to perform a veno-arterial (VA) technique of returning the blood to the artery (aorta) of the patient again. The extracorporeal circulator 1 is a device for assisting the heart and lungs. Hereinafter, a technique, in which after blood is removed from a patient and is subjected to predetermined treatment outside the body, the blood is fed into the body of the patient again, will be referred to as "extracorporeal circulation".

As illustrated in FIG. 1, the extracorporeal circulator 1 has a circulation circuit which causes blood to circulate. The circulation circuit includes the artificial lung 2, a centrifugal pump 3, a drive motor 4 which is driving means for driving the centrifugal pump 3, a vein side catheter (percutaneous catheter for blood removing) 5, an artery side catheter (catheter for blood feeding) 6, and a controller 10 which serves as a control unit.

The vein side catheter (catheter for blood removing) 5 is inserted through the femoral vein, and a distal end of the vein side catheter 5 indwells in the right atrium via the inferior vena cava. The vein side catheter 5 is connected to the centrifugal pump 3 via a blood removing tube (blood removing line) 11. The blood removing tube 11 is a conduit line for feeding blood.

The artery side catheter (catheter for blood feeding) 6 is inserted through the femoral artery.

When the drive motor 4 operates the centrifugal pump 3 in response to a command SG of the controller 10, the centrifugal pump 3 removes blood through the blood removing tube 11 and causes the blood to pass through the artificial lung 2. Thereafter, the centrifugal pump 3 can cause the blood to return to a patient P via a blood feeding tube (blood feeding line) 12.

The artificial lung 2 is disposed between the centrifugal pump 3 and the blood feeding tube 12. The artificial lung 2 exchanges gas (oxygenation and/or carbon dioxide removal) in blood. The artificial lung 2 is a membrane-type artificial lung, for example. It is particularly preferable to use a hollow fiber membrane-type artificial lung. Oxygen gas is supplied to the artificial lung 2 from an oxygen gas supply section 13 through a tube 14. The blood feeding tube 12 is a conduit line connecting the artificial lung 2 and the artery side catheter 6 to each other.

As the blood removing tube 11 and the blood feeding tube 12, for example, it is possible to use conduit lines made of a synthetic resin, such as a vinyl chloride resin or silicone rubber, which is highly transparent and flexible to be elastically deformable. Blood (liquid) flows in a V1-direction inside the blood removing tube 11, and blood flows in a V2-direction inside the blood feeding tube 12.

In the circulation circuit illustrated in FIG. 1, an ultrasound air bubble detection sensor 20 is disposed in the middle of the blood removing tube 11. A fast clamp 17 is disposed in the middle of the blood feeding tube 12.

In a case where an air bubble is incorporated into the circuit during extracorporeal circulation due to an erroneous operation of a three-way stopcock 18, damage to the tubes, and the like, the ultrasound air bubble detection sensor 20 detects the incorporated air bubble. In a case where the ultrasound air bubble detection sensor 20 detects that an air bubble is present in blood being fed to the inside of the blood removing tube 11, the ultrasound air bubble detection sensor 20 transmits a measurement signal of air bubble detection to the controller 10. The controller 10 sounds an alarm for notification based on this measurement signal, and the controller 10 lowers the rotational frequency of the centrifugal pump 3 or stops the centrifugal pump 3. Moreover, the controller 10 commands the fast clamp 17 such that the fast clamp 17 immediately closes the blood feeding tube 12. Accordingly, an air bubble is stopped from being fed to the inside of the body of the patient P. The controller 10 controls the operation of the extracorporeal circulator 1 to prevent an air bubble from being incorporated into the body of the patient P.

A pressure sensor is provided in the tube 11 (12, 19) of the circulation circuit of the extracorporeal circulator 1. For example, the pressure sensor can be mounted in any one or all of a mounting position A1 of the blood removing tube 11, a mounting position A2 of the blood feeding tube 12 of the circulation circuit, and a mounting position A3 of a connection tube 19 connecting the centrifugal pump 3 and the artificial lung 2 to each other. Accordingly, when extracorporeal circulation is performed with respect to the patient P using the extracorporeal circulator 1, the pressure inside the tube 11 (12, 19) can be measured by the pressure sensor. The mounting position of the pressure sensor is not limited to the mounting positions A1, A2, and A3 described above and can be mounted at any position in the circulation circuit.

First Embodiment

With reference to FIGS. 2 to 5, a percutaneous catheter assembly (which will hereinafter be referred to as a "catheter assembly") 100 according to a first embodiment of the present invention will be described. FIGS. 2 to 5 are views describing a configuration of the catheter assembly 100 according to the first embodiment.

Figure 2:
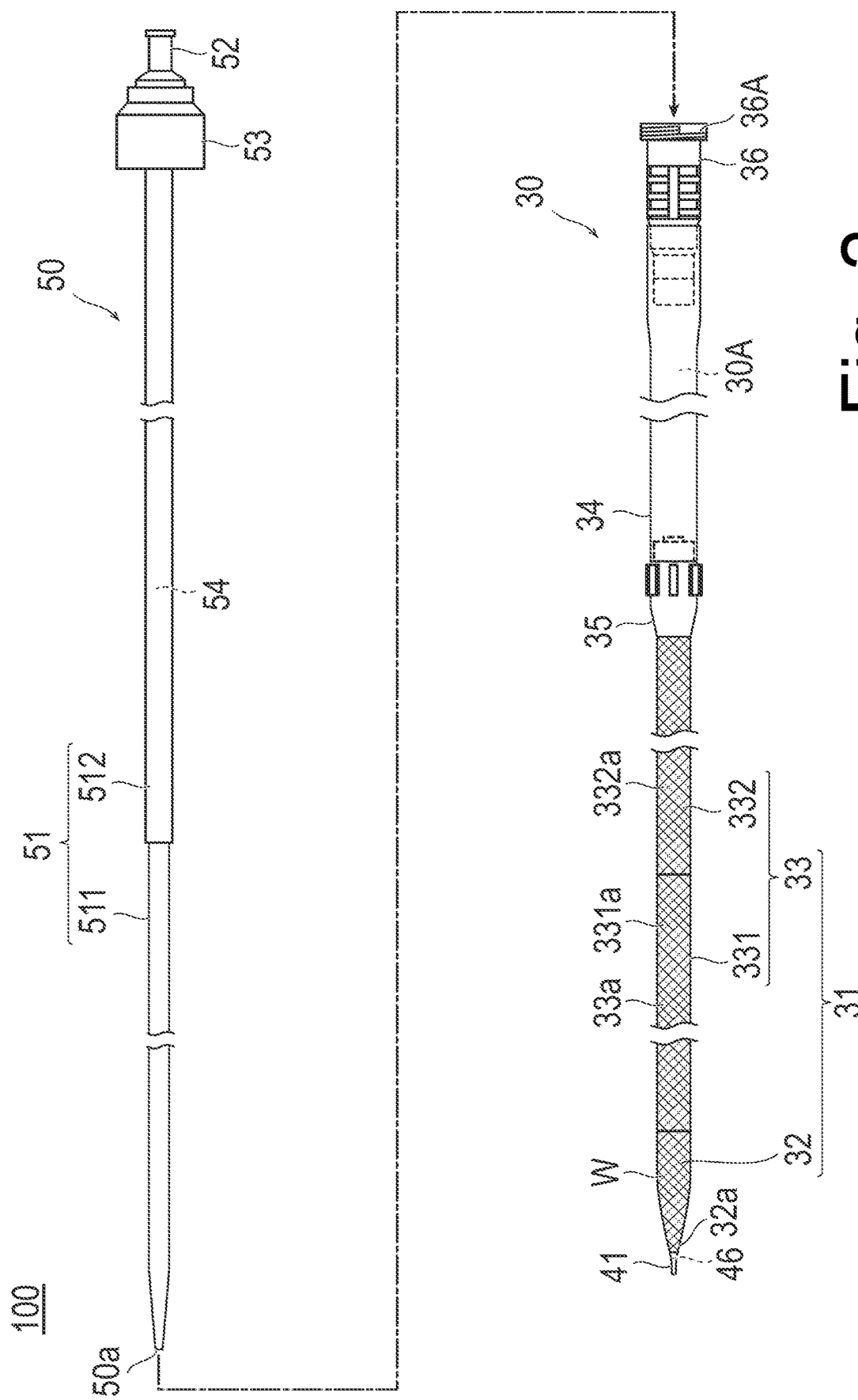
FIG. 2 is a side view illustrating a catheter assembly before a dilator is inserted through the inside of a catheter according to a first embodiment.

As illustrated in FIG. 2, the catheter assembly 100 according to the present embodiment has a percutaneous catheter (which will hereinafter be referred to as a "catheter") 30 through which blood passes, and a dilator 50 which is inserted through the catheter 30 in preparation for placement into a patient. The catheter 30 is used as the vein side catheter (catheter for blood removing) 5 in FIG. 1.

In this specification, a side inserted into a living body will be referred to as a "distal end" or a "distal side", and a hand-side operated by a practitioner will be referred to as a "proximal end" or a "proximal side". A distal portion denotes a certain range including the distal end (outermost distal end) and a surrounding area thereof, and a proximal portion denotes a certain range including the proximal end (innermost proximal end) and a surrounding area thereof.

As illustrated in FIG. 2, the catheter 30 according to the present embodiment has a catheter tube 31, a distal tip 41 which is disposed on the distal side of the catheter tube 31 and is configured to receive a distal end of the dilator 50, a clamping tube 34 which is disposed on the proximal side of the catheter tube 31, a catheter connector 35 which connects the catheter tube 31 and the clamping tube 34 to each other, and a lock connector 36 which is disposed on the proximal side of the clamping tube 34.

Figure 3:
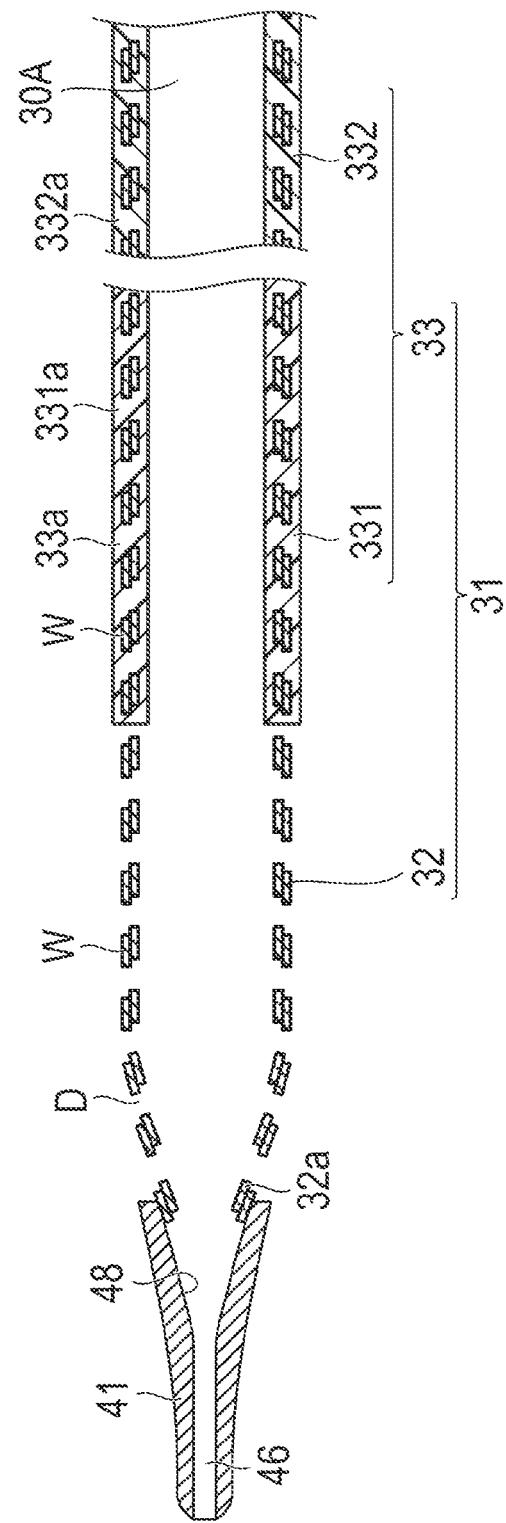
FIG. 3 is a sectional side view illustrating a part in the vicinity of a distal end of the catheter of FIG. 2.

As illustrated in FIGS. 2 and 3, the catheter 30 has a lumen 30A which penetrates the catheter 30 from the distal end to the proximal end and allows the dilator 50 to be inserted therethrough.

As illustrated in FIGS. 2 to 5, the catheter tube 31 has a non-coated axial portion 32 which is formed of wires W braided in an intersecting manner, and a coated axial portion 33 which is formed by coating (e.g., embedding) the wires W braided in an intersecting manner with a resin material 33a.

The non-coated portion 32 is configured to have the wires W uncovered. Therefore, the non-coated portion 32 is disposed on a blood removing target site inside a living body and is configured to be able to efficiently perform blood removal via gaps D among the wires W, as illustrated in FIG. 3 (refer to FIG. 6C).

As illustrated in FIGS. 2 and 3, a distal end 32a of the non-coated portion 32 is formed to have a tapered shape reduced in diameter toward the distal side and is internally held by the distal tip 41.

As illustrated in FIGS. 2 to 5, the coated portion 33 has a distal portion 331 provided on the distal side, and a proximal portion 332 provided on the proximal side of the distal portion 331.

As a resin material 332a provided in the proximal portion 332, a resin material having hardness higher than that of a resin material 331a provided in the distal portion 331 is used. Therefore, the proximal portion 332 is configured to have flexibility lower than that of the distal portion 331.

Figure 4:
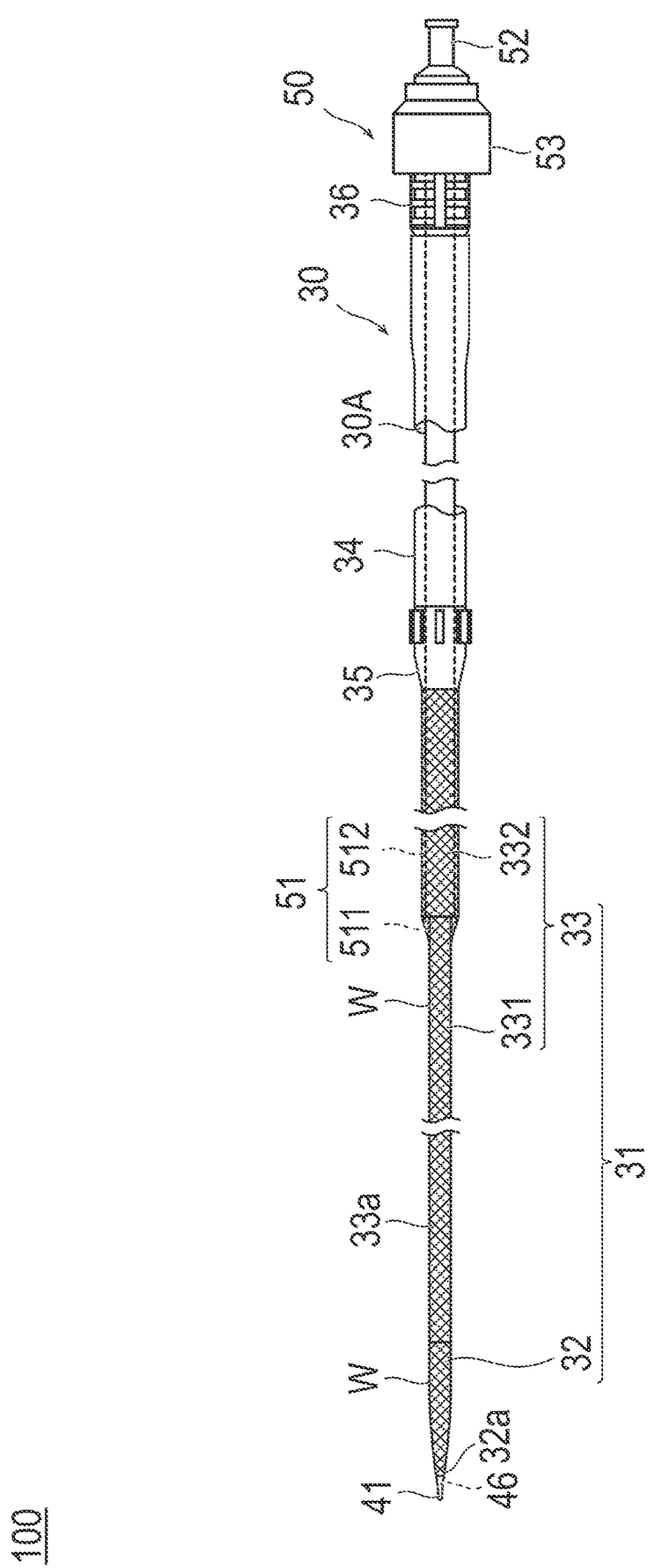
FIG. 4 is a side view illustrating the catheter assembly after the dilator is inserted through the inside of the catheter of FIG. 2.
Figure 5:
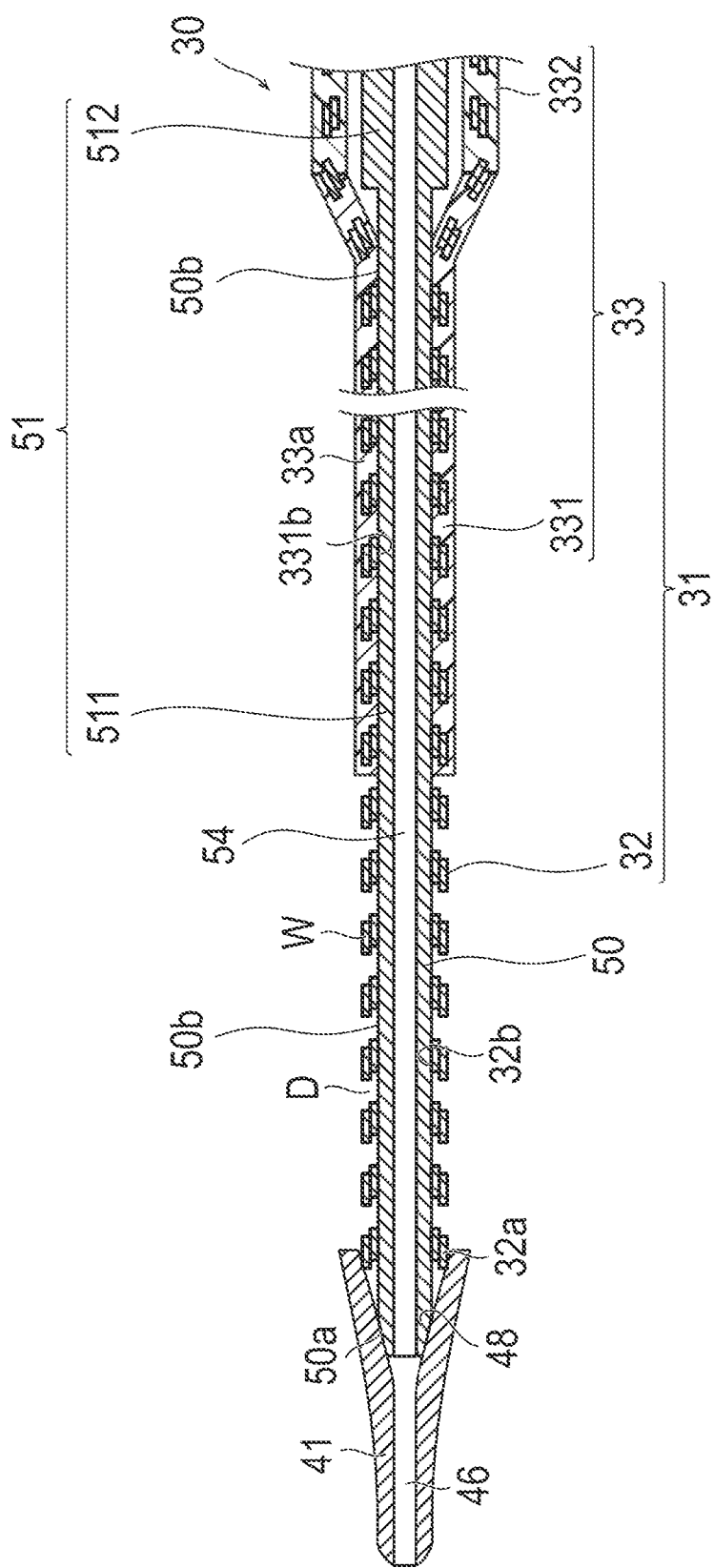
FIG. 5 is a sectional side view illustrating a part in the vicinity of a distal end of the catheter assembly after the dilator is inserted through the inside of the catheter of FIG. 2.

According to the catheter 30 having such a configuration, due to the dilator 50 inserted therethrough, as illustrated in FIGS. 4 and 5, the non-coated portion 32 and the distal portion 331 expand in an axial direction, and the inner diameters and the outer diameters of the non-coated portion 32 and the distal portion 331 are reduced in diameter.

In addition, as illustrated in FIGS. 2 and 3, the coated portion 33 is constituted such that the inner diameter and the outer diameter are substantially the same as the diameter of the non-coated portion 32 before the dilator 50 is inserted through the catheter 30.

The lengths of the non-coated portion 32, the high flexibility distal portion 331, and the low flexibility proximal portion 332 are configured to be lengths required for the non-coated portion 32 to be disposed at a desired blood removing target. The length of the non-coated portion 32 ranges from 1 to 10 cm, for example, the length of the distal portion 331 ranges from 20 to 34 cm, for example, and the length of the proximal portion 332 ranges from 15 to 20 cm, for example.

In the present embodiment, the blood removing target is a right atrium. The catheter 30 is inserted into a living body such that the non-coated portion 32 is disposed in the right atrium, and the catheter 30 indwells therein.

In a state where the non-coated portion 32 is disposed on the blood removing target, the non-coated portion 32 and the distal portion 331 are disposed in the inferior vena cava that is a comparatively wide blood vessel, and the proximal portion 332 is disposed in the femoral vein that is a comparatively narrow blood vessel.

In addition, if the dilator 50 is inserted through the lumen 30A of the catheter 30, the non-coated portion 32 and the distal portion 331 having high flexibility expand in the axial direction and are accordingly reduced in inner diameter and outer diameter, as illustrated in FIGS. 4 and 5. In this configuration, as illustrated in FIG. 5, an inner peripheral portion 32b of the non-coated portion 32 and an inner peripheral portion 331b of the distal portion 331 come into tight contact with an outer peripheral portion 50b of the dilator 50. Since the catheter 30 is inserted into a living body in this state, the catheter 30 can be inserted in a low invasive manner.

In addition, if the dilator 50 is withdrawn from the lumen 30A of the catheter 30 after the catheter 30 indwells inside a living body, the non-coated portion 32 and the distal portion 331 contract from the state of expanding in the axial direction, as illustrated in FIGS. 2 and 3, and the inner diameters and the outer diameters of the non-coated portion 32 and the distal portion 331 are radially increased. At this time, the inner diameters of the non-coated portion 32 and the distal portion 331 are configured to be larger than the outer diameter of the dilator 50. In addition, when the dilator 50 is withdrawn from the lumen 30A of the catheter 30, it is preferable that the non-coated portion 32 and the distal portion 331 do not come into tight contact with any vascular wall. According to the catheter 30 having such a configuration, blood can be efficiently removed through the non-coated port ion 32.

Here, the pressure loss in a lumen of each of the non-coated portion 32 and the distal portion 331 is obtained by multiplying the entire length of each of the non-coated portion 32 and the distal portion 331 by the (average) cross-sectional area of the passage, respectively. That is, the pressure losses inside the non-coated portion 32 and the distal portion 331 are reduced during blood removal by increasing the inner diameters of the non-coated portion 32 and the distal portion 331. If the pressure losses inside the non-coated portion 32 and the distal portion 331 are reduced, the flow rate of blood flowing in the circulation circuit is accordingly increased. In order to obtain a sufficient circulation amount of blood, the inner diameters of the non-coated portion 32 and the distal portion 331 are required to be increased.

On the other hand, in a case where the tube thicknesses are substantially uniform, if the inner diameters of the non-coated portion 32 and the distal portion 331 are increased, the outer diameters are increased and would remain increased without adopting the present invention. Therefore, when the catheter 30 is inserted into a living body with the increased outer diameters, a load to a patient increases, thereby being a hindrance to a low-invasive technique.

From the viewpoint described above, the inner diameter of the catheter tube 31 before the dilator 50 is inserted through the catheter 30 can range from 4 to 11 mm, for example. In addition, the thickness the catheter tube 31 can range from 0.4 to 0.6 mm, for example.

In the present embodiment, the wires W are formed of a shape memory material, such as a known shape memory metal or a known shape memory resin. As a shape memory metal, for example, a titanium-based alloy (Ni—Ti, Ti—Pd, Ti—Nb—Sn, or the like) or a copper-based alloy can be used. In addition, as a shape memory resin, for example, an acryl-based resin, a trans-isoprene polymer, polynorbornene, styrene-butadiene copolymer, and polyurethane can be used.

Since the wires W are formed of a shape memory material, contraction distances of the non-coated portion 32 and the distal portion 331 in the axial direction when the dilator 50 is withdrawn from the catheter 30 are the same as expansion distances of the non-coated portion 32 and the distal portion 331 in the axial direction when the dilator 50 is inserted through the catheter 30.

In addition, it is preferable that wire diameter of the wires W range from 0.08 mm to 0.2 mm.

It is possible to suitably exhibit a function as a reinforcement body improving strength by setting the wire diameter of the wires W to 0.08 mm or larger.

On the other hand, the thickness of the coated portion 33 can be 0.5 mm or smaller and the inner diameter can be increased while having the small outer diameter by setting the wire diameter of the wires W to 0.2 mm or smaller. Therefore, it is possible to realize both minimizing a load to the body of a patient when the catheter 30 is inserted and then reducing a pressure loss during blood flow. In addition, at this time, even at a location where the wires W are braided in a two-layer state, the wires W can be prevented from being uncovered from the resin material 33a. For example, the wire W has a circular cross-section. However, the cross-sectional shape is not limited thereto and may be a rectangular shape, a square shape, an elliptical shape, or the like.

The resin material 33a may be formed by using vinyl chloride, silicon, polyethylene, nylon, urethane, polyurethane, a fluororesin, a thermoplastic elastomer resin, or the like, or by using a composite material thereof.

A silicon raw material has an advantage in that a blood vessel is unlikely to be damaged, due to high biocompatibility and softness of the raw material itself. A polyethylene raw material is soft and has hardness to withstand a pressure. Moreover, a polyethylene raw material has biocompatibility equivalent to a silicon raw material. A polyethylene raw material has an advantage of being harder than silicon and being easily inserted into a narrow blood vessel. In addition, a polyurethane raw material has an advantage of being soft after insertion. As the resin material 33a, it is possible to use a material which can be applied by utilizing the advantages of these raw materials.

In addition, a polyurethane raw material may be subjected to hydrophilic coating. In this case, the tube surface is smooth, is easily inserted into a blood vessel, and is unlikely to damage a vascular wall. Blood or protein is unlikely to adhere to the tube surface, so that it is possible to expect to prevent a thrombus from being formed.

A method of forming the catheter tube 31 is not particularly limited. However, for example, the catheter tube 31 can be formed by dip coating (immersion method) or insert molding.

As illustrated in FIG. 2, the distal tip 41 is disposed on the distal side of the non-coated portion 32. The distal tip 41 has a tapered shape gradually reduced in diameter toward the distal side. As illustrated in FIG. 3, the distal tip 41 internally holds the distal end 32a of the non-coated portion 32.

As illustrated in FIGS. 3 and 5, the distal tip 41 has a through-hole 46 which allows a guide wire (not illustrated) to be inserted through the inside thereof. A tapered receiving surface 48 to capture a distal surface 50a of the dilator 50 is formed inside the distal tip 41. For example, the distal tip 41 can be formed of a hard plastic.

The non-coated portion 32 can be effectively prevented from being squashed at the time of blood removal by fixing the hard distal tip 41 to the distal end of the non-coated portion 32.

As illustrated in FIGS. 2 and 4, the clamping tube 34 is provided on the proximal side of the catheter tube 31. A lumen allowing the dilator 50 to be inserted therethrough is provided on the inner side of the clamping tube 34. The clamping tube 34 can be formed by using a material similar to that of the catheter tube 31.

As illustrated in FIGS. 2 and 4, the catheter connector 35 connects the catheter tube 31 and the clamping tube 34 to each other. A lumen allowing the dilator 50 to be inserted therethrough is provided on the inner side of the catheter connector 35.

As illustrated in FIGS. 2 and 4, the lock connector 36 is connected to the proximal side of the clamping tube 34. A lumen allowing the dilator 50 to be inserted therethrough is provided on the inner side of the lock connector 36. As illustrated in FIG. 2, a male screw portion 36A provided with screw threads is provided on the outer surface of the lock connector 36 on the proximal side.

Next, a configuration of the dilator 50 will be described.

As illustrated in FIG. 2, the dilator 50 has a dilator tube 51 which is provided to extend in the axial direction, a dilator hub 52 to which a proximal end of the dilator tube 51 is fixed, and a screw ring 53 which is provided at a distal end of the dilator hub 52.

The dilator tube 51 is an elongated body extending in the axial direction and having comparatively high rigidity. The entire length of the dilator tube 51 in the axial direction is configured to be longer than the entire length of the catheter 30 in the axial direction. As illustrated in FIGS. 2 and 5, the dilator tube 51 includes a guide wire lumen 54 allowing a guide wire (not illustrated) to be inserted therethrough. The dilator tube 51 is guided by the guide wire and is inserted into a living body together with the catheter 30. After the catheter 30 indwells inside a living body, the dilator tube 51 is withdrawn from the catheter 30 by drawing out the dilator hub 52 to the proximal side.

As illustrated in FIG. 2, the dilator tube 51 has a small diameter portion 511 which is provided on the distal side, and a large diameter portion 512 which is provided on the proximal side of the small diameter portion 511 and has an outer diameter larger than that of the small diameter portion 511.

When the dilator 50 is fully inserted through the catheter 30, as illustrated in FIGS. 4 and 5, the small diameter portion 511 comes into tight contact with the inner peripheral portion 32b of the non-coated portion 32 and the inner peripheral portion 331b of the distal portion 331. In addition, when the dilator 50 is inserted through the catheter 30, the large diameter portion 512 is disposed in the inner circumference of the proximal portion 332.

The outer diameter of the small diameter portion 511 can range from 2 to 4 mm, for example. In addition, the outer diameter of the large diameter portion 512 can range from 3 to 10 mm, for example.

As illustrated in FIGS. 2 and 5, the dilator tube 51 includes the distal surface 50a which engages the receiving surface 48 of the distal tip 41. The dilator tube 51 has comparatively high rigidity and has resilience such that a thrusting force by an operation at hand to the distal side can be transmitted to the distal tip 41. Therefore, the dilator tube 51 plays a role of widening a narrow blood vessel by causing the distal surface 50a thereof to be attached to the receiving surface 48 of the distal tip 41 such that the distal tip 41 is thrust to the distal side.

The screw ring 53 has a female screw portion (not illustrated) in which a screw groove is provided on the inner surface of a lumen. The dilator 50 is configured to be attachable with respect to the catheter 30 by screwing the female screw portion of the screw ring 53 to the male screw portion 36A of the lock connector 36.

Method of Using Catheter

Figure 6:
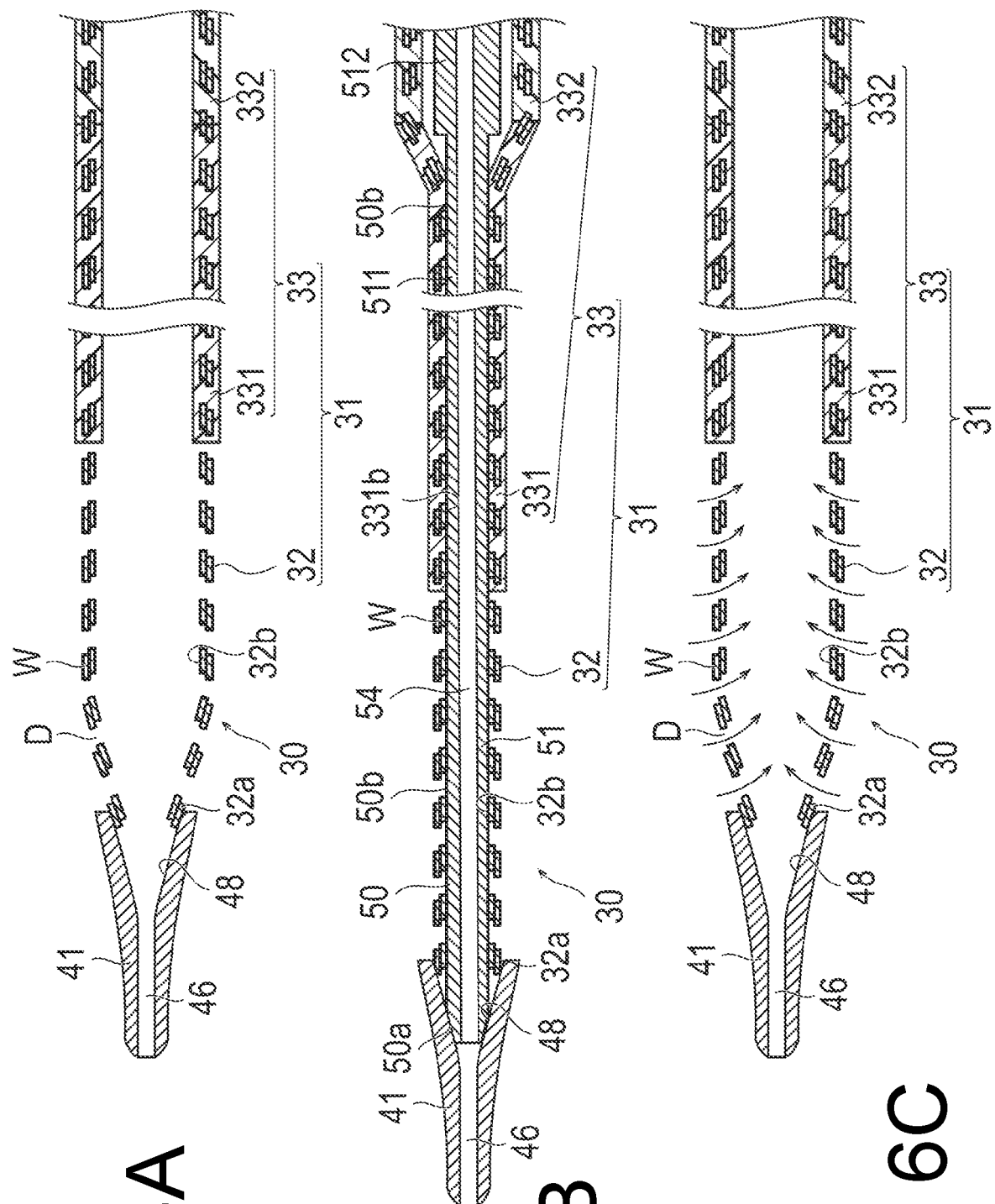
FIGS. 6A, 6B, and 6C are sectional side views for describing a method of using the catheter assembly according to the first embodiment.

Next, with reference to FIG. 6, a method of using the catheter assembly 100 described above will be described. FIG. 6A illustrates a state before the dilator 50 is inserted through the catheter 30, FIG. 6B illustrates a state after the dilator 50 is fully inserted through the catheter 30, and FIG. 6C illustrates a state where the dilator 50 is fully withdrawn from the catheter 30 and blood is removed through the non-coated portion 32, respectively.

First, a practitioner inserts the dilator tube 51 of the dilator 50 through the catheter 30 illustrated in FIG. 6A. The dilator tube 51 passes through the insides of the coated portion 33 and the non-coated portion 32 sequentially, and the distal surface 50a of the dilator 50 engages the receiving surface 48 of the distal tip 41.

Here, as illustrated in FIG. 2, the entire length of the dilator tube 51 in the axial direction is configured to be longer than the entire nominal (i.e., relaxed) length of the catheter 30 in the axial direction. Therefore, in a state where the distal surface 50a of the dilator 50 engages the receiving surface 48 of the distal tip 41, the distal tip 41 is pressed to the distal side. Accordingly, the distal end 32a of the non-coated portion 32 which is fixed to the distal tip 41 is pulled to the distal side. Accordingly, the catheter 30 receives a force of expansion in the axial direction, and the non-coated portion 32 and the distal portion 331 having high flexibility in the catheter 30 become elongated in the axial direction, as illustrated in FIG. 6B. Thereafter, the proximal end of the catheter 30 is fixed to the dilator hub 52. At this time, the non-coated portion 32 and the distal portion 331 expand in the axial direction, the inner diameters and the outer diameters are reduced, and the inner peripheral portion 32b of the non-coated portion 32 and the inner peripheral portion 331b of the distal portion 331 come into tight contact with the outer peripheral portion 50b of the dilator 50.

Next, the catheter 30, through which the dilator 50 is inserted, is inserted along a guide wire (not illustrated) which has been inserted into a target site inside a living body by the practitioner in advance. At this time, since the dilator 50 is inserted through the catheter 30, the outer diameters of the non-coated portion 32 and the distal portion 331 are reduced, the catheter 30 can be inserted into a living body in a low invasive manner, and a load to the body of a patient can be minimized.

In addition, the catheter 30 is inserted into a living body until the non-coated portion 32 is disposed in the right atrium, and the catheter 30 indwells therein. In a state where the non-coated portion 32 is disposed on the blood removing target, the non-coated portion 32 and the distal portion 331 are disposed in the inferior vena cava that is a comparatively wide blood vessel, and the proximal portion 332 is disposed in the femoral vein that is a comparatively narrow blood vessel.

Next, the dilator 50 and the guide wire are withdrawn from the catheter 30. At this time, the dilator tube 51 and the guide wire are temporarily pulled to the location of the clamping tube 34 of the catheter 30 and are clamped by forceps (not illustrated). Thereafter, the dilator tube 51 and the guide wire are completely withdrawn from the catheter 30. Since the dilator tube 51 is withdrawn from the catheter 30, the catheter 30 is released from a force which is received from the dilator 50 that had been expanding it in the axial direction. Therefore, as illustrated in FIG. 6C, the non-coated portion 32 and the distal portion 331 contract in the axial direction, and the inner diameters and the outer diameters of the non-coated portion 32 and the distal portion 331 are increased. Accordingly, the pressure losses inside the non-coated portion 32 and the distal portion 331 can be reduced and the required flow rate of liquid can be ensured.

Next, the lock connector 36 of the catheter 30 is connected to the blood feeding tube 12 of the extracorporeal circulator in FIG. 1. After it is checked that connection of the catheter on the blood feeding side is completed, the forceps on the clamping tube 34 are released, and extracorporeal circulation starts.

When extracorporeal circulation ends, the catheter 30 is withdrawn from the blood vessel, and the insertion location is subjected to hemostatic restoration by a surgical technique as necessary.

As described above, in summary, a method of using the catheter 30 according to the present embodiment includes (i) a tight contact step of causing the inner peripheral portions of the non-coated portion and the distal portion to come into tight contact with the outer peripheral portion of the dilator by inserting the dilator through the inside of the catheter and expanding the non-coated portion and the distal portion in the axial direction such that the inner diameters are reduced, (ii) an insertion step of inserting the catheter, in a state where the inner peripheral portions of the non-coated portion and the distal portion are in tight contact with the outer peripheral portion of the dilator, into a living body, and (iii) a withdrawing step of withdrawing the dilator from the inside of the catheter.

As described above, the catheter 30 according to the present embodiment is a catheter 30 through which blood passes and which expands in the axial direction due to the dilator 50 inserted therethrough. The catheter 30 has the catheter tube 31 that extends in the axial direction, and the distal tip 41 that is provided on the distal side of the catheter tube 31 and is configured to allow the dilator 50 to be attached thereto. The catheter tube 31 includes the non-coated portion 32 which is provided on the proximal side of the distal tip 41 and is formed of the wires W braided in an intersecting manner, and the coated portion 33 which is provided on the proximal side of the non-coated portion 32 and is formed by coating the wires W braided in an intersecting manner with the resin material 33a. The braided wires W preferably forma mesh wherein a plurality of wires are braided in a reticulated (e.g., helical) manner along a cylindrical surface to provide regular gaps D between the wires. The inner diameter of the non-coated portion 32 is configured to be larger than the outer diameter of the dilator 50 before the dilator 50 is inserted through the catheter 30. When the dilator 50 is inserted through the catheter 30, the non-coated portion 32 expands in the axial direction and is reduced in inner diameter so that the inner peripheral portion 32b of the non-coated portion 32 comes into tight contact with the outer peripheral portion 50b of the dilator 50. According to the catheter 30 having such a configuration, if the dilator 50 is inserted through the catheter 30, the inner peripheral portion 32b of the non-coated portion 32 comes into tight contact with the outer peripheral portion 50b of the dilator 50. Therefore, the outer diameter of the non-coated portion 32 is reduced. It is possible to minimize a load to the body of a patient by inserting the catheter 30 into a living body in this state. In addition, if the dilator 50 is withdrawn from the catheter 30 after the catheter 30 indwells inside a living body, the catheter tube 31 contracts in the axial direction and returns to the original state. At this time, since the inner diameter of the non-coated portion 32 is larger than the outer diameter of the dilator 50, a pressure loss in the non-coated portion 32 can be reduced, so that a required flow rate of liquid can be ensured.

In addition, the coated portion 33 has the distal portion 331 which is provided on the distal side, and the proximal portion 332 which is provided on the proximal side of the distal portion 331 and has flexibility lower than that of the distal portion 331. The inner diameter of the distal portion 331 is configured to be larger than the outer diameter of the dilator 50 before the dilator 50 is inserted through the catheter 30. When the dilator 50 is inserted through the catheter 30, the distal portion 331 expands in the axial direction and is reduced in inner diameter so that the inner peripheral portion 331b of the distal portion 331 comes into tight contact with the outer peripheral portion 50b of the dilator 50. Therefore, the non-coated portion 32 and the distal portion 331 configured to be highly flexible expand in the axial direction and are reduced in outer diameter by inserting the dilator 50 through the catheter 30. Accordingly, the catheter 30 can be more easily inserted into a living body in a low invasive manner. In addition, if the dilator 50 is withdrawn from the catheter 30, the non-coated portion 32 and the distal portion 331 contract in the axial direction, the inner diameters of the non-coated portion 32 and the distal portion 331 are increased. Accordingly, the pressure losses inside the non-coated portion 32 and the distal portion 331 can be reduced.

In addition, the distal end 32a of the non-coated portion 32 is formed to have a tapered shape reduced in diameter toward the distal side, and the distal tip 41 internally holds the distal end 32a of the non-coated portion 32. Therefore, in a simple configuration, the distal tip 41 is fixed to the distal end 32a of the non-coated portion 32.

In addition, the wires W are preferably formed of a shape memory material. Therefore, when the dilator 50 is withdrawn from the catheter 30, the catheter tube 31 contracts in the axial direction and is increased in inner diameter and outer diameter, thereby suitably returning to the original shape. Therefore, a pressure loss can be more suitably reduced.

In addition, as described above, the catheter assembly 100 according to the present embodiment has the catheter 30 described above, and the dilator 50. According to this configuration, a load to the body of a patient can be minimized, a pressure loss of liquid circulating in a circulation circuit can be reduced, and a required flow rate of the liquid can be ensured.

Modification Example 1 of First Embodiment

Next, Modification Example 1 of the first embodiment will be described.

The catheter according to the first embodiment described above is used as the vein side catheter (catheter for blood removing) 5 in FIG. 1. In contrast, a catheter according to Modification Example 1 is used as the artery side catheter 6 (catheter for blood feeding) in FIG. 1. The catheter according to Modification Example 1 can have the same construction and configuration as that of the catheter according to the first embodiment.

In the catheter according to Modification Example 1, the non-coated portion 32 is configured to be subcutaneously placed into a blood feeding target inside a living body such that blood feeding (e.g., returning of oxygenated blood from a perfusion device) can be efficiently performed via the gaps D of the wires W.

For example, in a case of a configuration in which the catheter tube is coated with a resin material to the distal end and blood feeding is performed through only a through-hole at a distal tip, the flow velocity of blood fed through the through-hole becomes comparatively high due to the narrow diameter of the through-hole, so that there is concern for the influence on a blood vessel. In contrast, according to the catheter according to Modification Example 1, blood feeding is performed via many gaps D provided in the non-coated portion 32. Therefore, the flow velocity of blood fed through the gaps D becomes comparatively low. Therefore, an influence on a blood vessel can be reduced and safety can be improved.

Modification Example 2 of First Embodiment

Next, Modification Example 2 of the first embodiment will be described.

Figure 7:
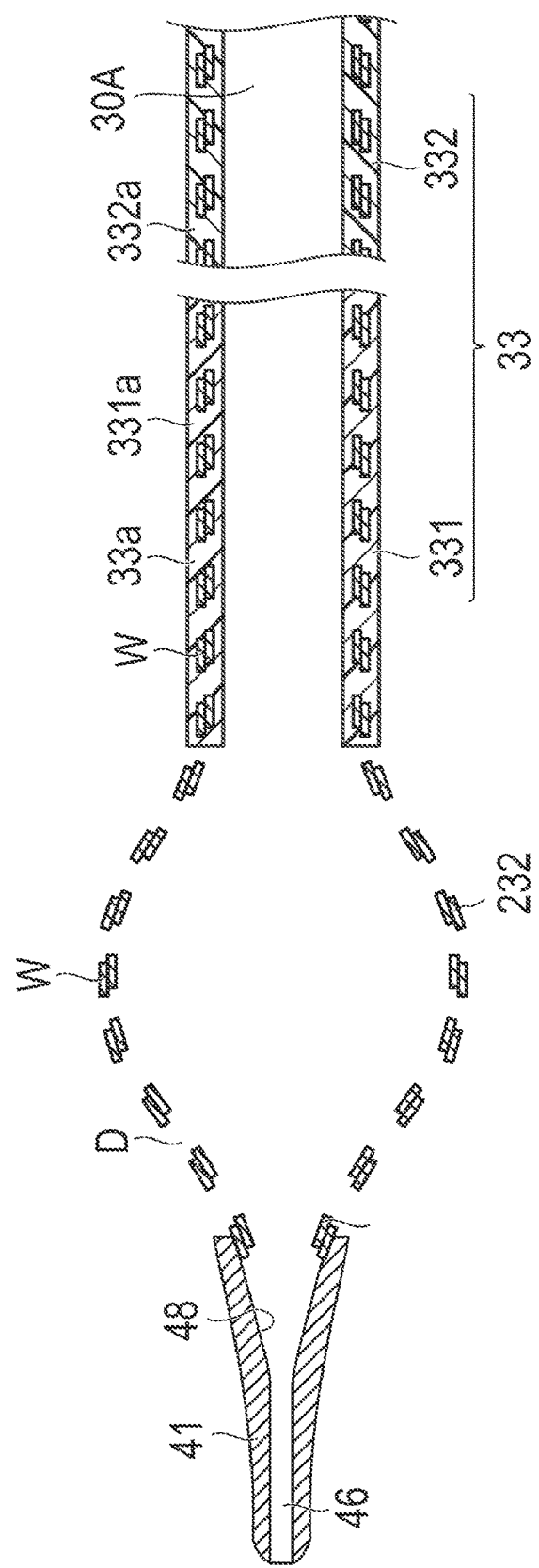
FIG. 7 is a sectional side view illustrating a catheter according to a modification of the first embodiment.

In a catheter 90 according to Modification Example 2, as illustrated in FIG. 7, the inner diameter and the outer diameter of a non-coated portion 232 before the dilator 50 is fully inserted through the catheter 30 have a nominal (i.e., relaxed) state larger than the inner diameter and the outer diameter of the coated portion 33.

According to the catheter 90 having such a configuration, if the dilator 50 is inserted through the catheter 90, the inner peripheral portion of the non-coated portion 232 comes into tight contact with the outer peripheral portion 50b of the dilator 50 (refer to FIG. 6B). Therefore, the outer diameter of the non-coated portion 232 is reduced prior to insertion in the body. It is possible to minimize a load to the body of a patient by inserting the catheter 90 into a living body in this state. In addition, if the dilator 50 is withdrawn from the catheter 90 after the catheter 90 indwells inside a living body, the non-coated portion 232 contracts in the axial direction and returns to the original state. At this time, since the inner diameter and the outer diameter of the non-coated portion 232 according to Modification Example 2 are larger than the inner diameter and the outer diameter of the coated portion 33, a pressure loss in the non-coated portion 232 is further reduced compared to the catheter 30 according to the first embodiment, so that a required flow rate of liquid can be more suitably ensured.

The inner diameter and the outer diameter of the non-coated portion 232 may be configured to be radially larger (at least at some axial positions) than the inner diameter and the outer diameter of the coated portion 33.

Second Embodiment

Figure 8:
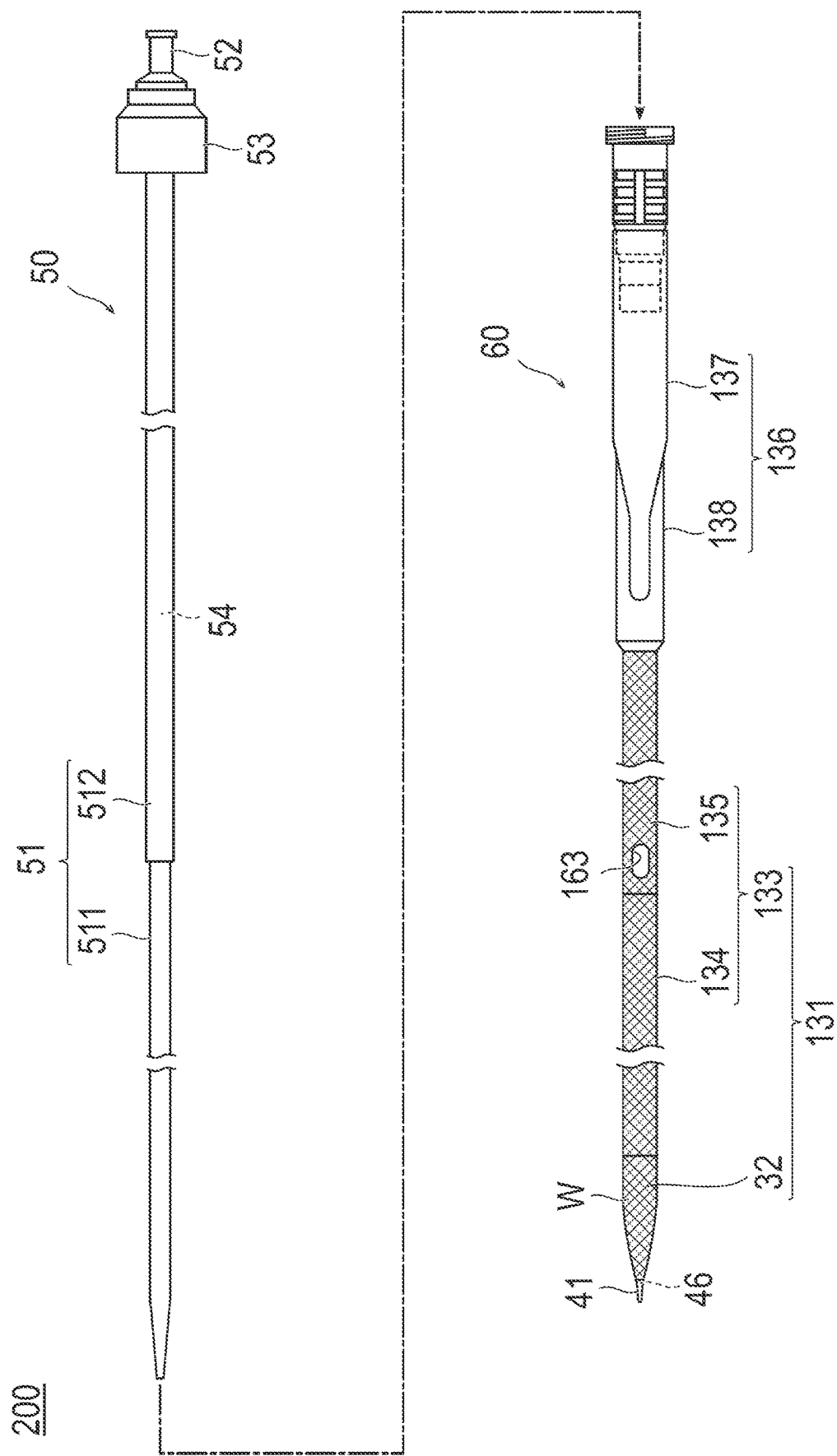
FIG. 8 is a plan view illustrating a catheter assembly before the dilator is inserted through the inside of a catheter according to a second embodiment.
Figure 9:
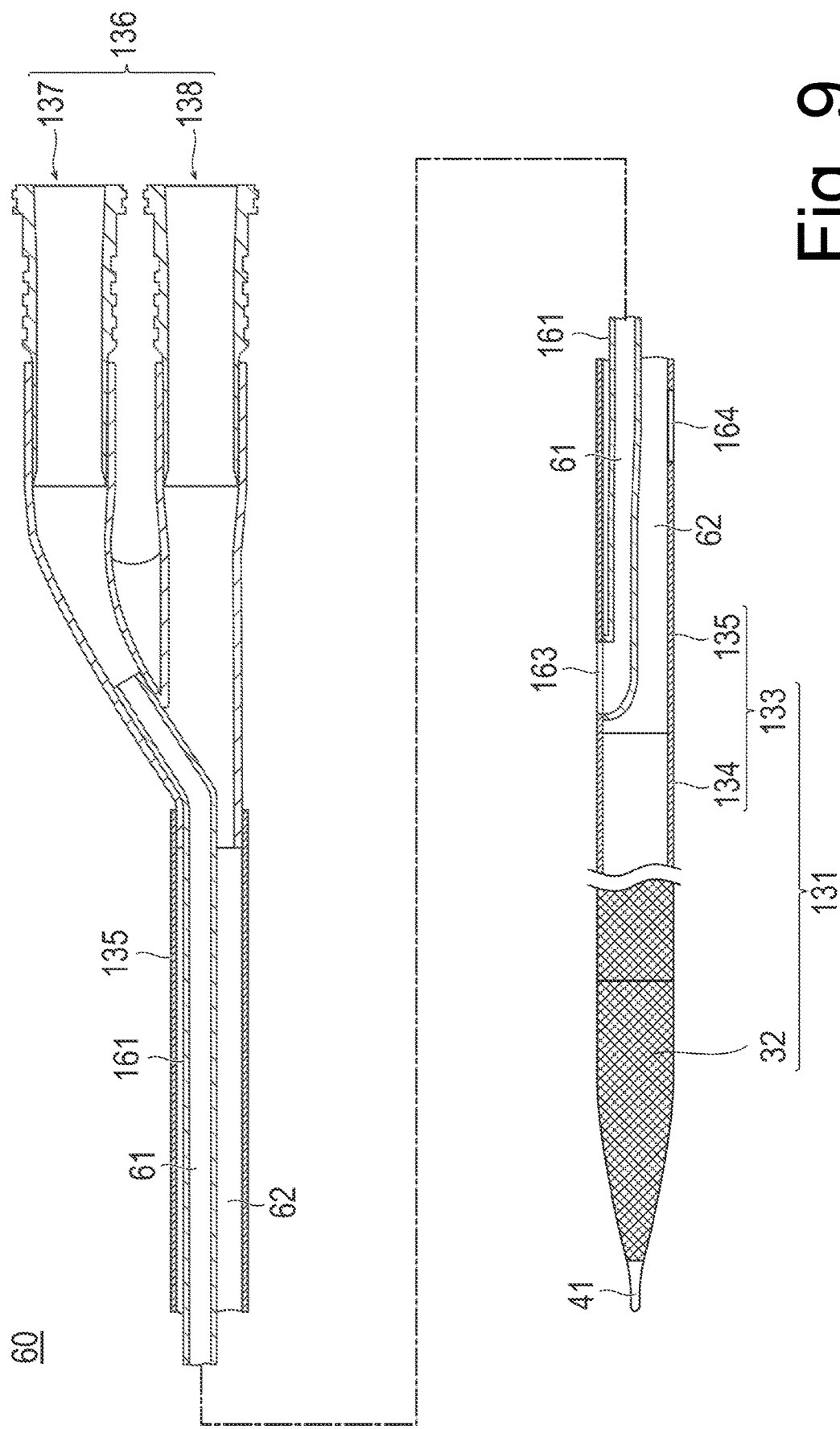
FIG. 9 is a part of a sectional view illustrating the catheter according to the second embodiment.
Figure 10:
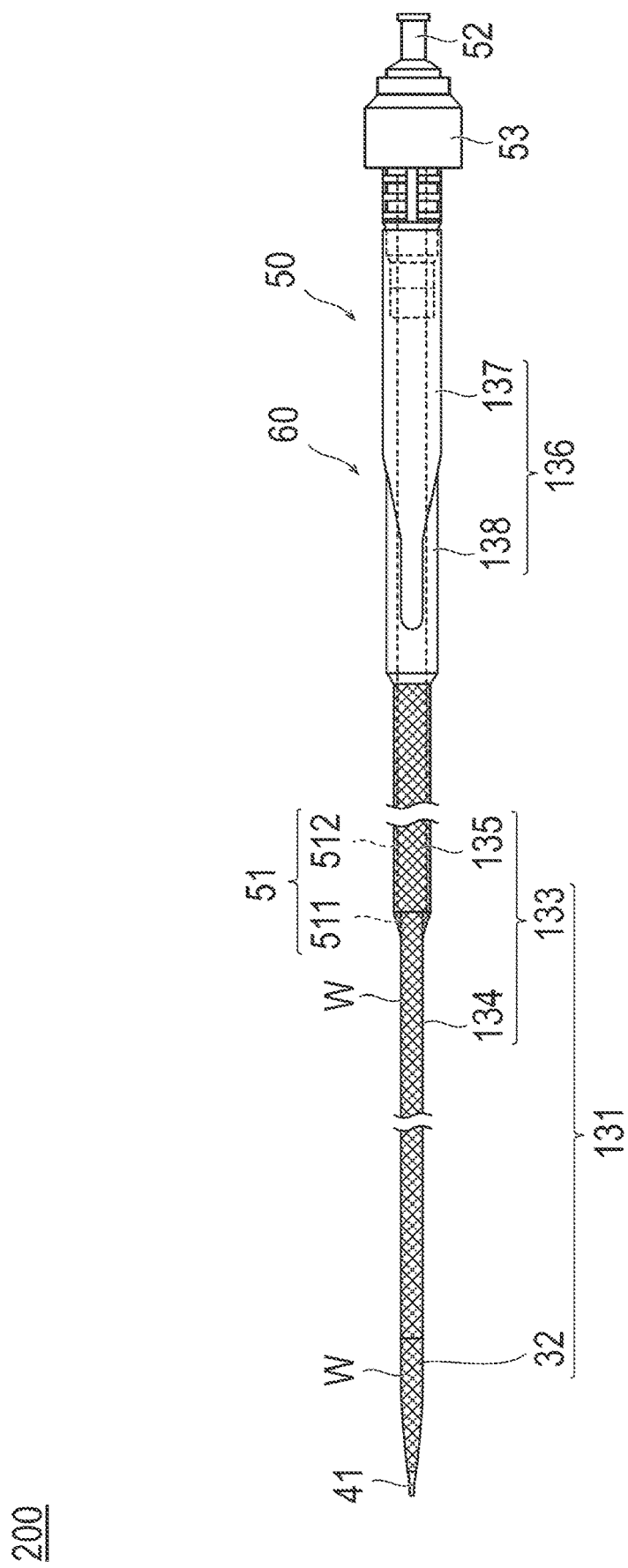
FIG. 10 is a plan view illustrating the catheter assembly after the dilator inserted through the inside of the catheter according to the second embodiment.

Next, with reference to FIGS. 8 to 10, a percutaneous catheter assembly (which will hereinafter be referred to as a "catheter assembly") 200 according to a second embodiment of the present invention will be described. FIGS. 8 to 10 are views describing the configuration of the catheter assembly 200 according to the second embodiment.

As illustrated in FIG. 8, the catheter assembly 200 according to the second embodiment has a percutaneous catheter (which will hereinafter be referred to as a "catheter") 60 for causing blood to pass therethrough, and the dilator 50 inserted through the catheter 60. Since the configuration of the dilator 50 is similar to the configuration in the first embodiment, description thereof will be omitted. Hereinafter, the catheter 60 will be described.

The catheter 60 is a so-called double lumen catheter, which can perform both blood feeding and blood removing at the same time. Therefore, in the present embodiment, for the extracorporeal circulator in FIG. 1, a technique is performed by using only one catheter 60, without using two catheters, that is, the vein side catheter (catheter for blood removing) 5 and the artery side catheter (catheter for blood feeding) 6.

As illustrated in FIG. 9, the catheter 60 according to the present embodiment differs from the catheter 30 according to the first embodiment in that an inner tube 161 including a first lumen 61 communicating with a side hole 163 for blood feeding has a double tube structure disposed in the lumen of a proximal portion 135.

According to the catheter 60, the pump of the extracorporeal circulator is operated to remove blood from the vein (vena cava) of a patient, and the blood is oxygenated by exchanging gas in the blood using an artificial lung. Thereafter, it is possible to perform a veno-venous (VV) artificial lung extracorporeal blood circulation of returning the blood to the vein (vena cava) of the patient again.

Hereinafter, each of the configurations of the catheter 60 will be described. Description of parts in common with those in the first embodiment is omitted, and only the characterized portions of the second embodiment will be described. In addition, the same reference signs are applied to the same portions as those of the first embodiment in description, and duplicated description thereof will be omitted.

As illustrated in FIGS. 8 to 10, the catheter 60 has a catheter tube 131, the distal tip 41 disposed on the distal side of the catheter tube 131, and the inner tube 161 disposed in the lumen of the catheter tube 131. Since the configuration of the distal tip 41 is the same as the configuration of the catheter 30 in the first embodiment, description thereof will be omitted.

As illustrated in FIGS. 8 and 9, the catheter tube 131 has the non-coated portion 32 which is formed of the wires W braided in an intersecting manner, and a coated portion 133 which is formed by coating the wires W braided in an intersecting manner with a resin material. In FIG. 9, a part of the catheter tube 131 is simply illustrated in a front view. Since the configuration of the non-coated portion 32 is the same as the configuration of the catheter 30 in the first embodiment, description thereof will be omitted.

As illustrated in FIGS. 8 and 9, the coated portion 133 has a distal portion 134 which is provided on the distal side, and the proximal portion 135 which is provided on the proximal side of the distal portion 134 and is configured to have flexibility lower than that of the distal portion 134.

As illustrated in FIG. 9, the proximal portion 135 has the side hole 163 for blood feeding provided at the distal end of the proximal portion 135, and a side hole 164 for blood removing provided on the proximal side of the side hole 163 for blood feeding. The side hole 163 for blood feeding and the side hole 164 for blood removing are configured to have an elliptic shape.

As illustrated in FIG. 9, the catheter 60 has the first lumen 61 which functions as a blood feeding path, and a second lumen 62 which functions as a blood removing path.

The first lumen 61 is formed in the lumen of the inner tube 161. The second lumen 62 is formed in the lumens of the non-coated portion 32 and the coated portion 133 and penetrates the lumens from the distal end to the proximal end.

The inner tube 161 is inserted into the second lumen 62 from the proximal side of the proximal portion 135 and is interlocked with the side hole 163 for blood feeding.

The side hole 163 for blood feeding is disposed on a blood feeding target inside a living body, and blood oxygenated by an artificial lung is fed into a living body via the side hole 163 for blood feeding.

The non-coated portion 32 and the side hole 164 for blood removing are configured to be disposed on different blood removing targets inside a living body such that blood can be efficiently removed. In addition, even if the non-coated portion 32 or the side hole 164 for blood removing is adsorbed to a vascular wall and is blocked, blood can be removed through a side which is not blocked. Therefore, extracorporeal circulation can be stably performed.

In the present embodiment, the catheter 60 is inserted through the internal jugular vein of the neck, and the distal end indwells in the inferior vena cava via the upper vena cava and the right atrium. The blood feeding target is the right atrium, and there are two blood removing targets, that is, the upper vena cava and the inferior vena cava.

As illustrated in FIG. 10, in a state of having the dilator 50 fully inserted, the catheter 60 is inserted into a living body and indwells therein such that the non-coated portion 32 is disposed in the inferior vena cava and the side hole 164 for blood removing is disposed in the internal jugular vein.

In a state where the non-coated portion 32 and the side hole 164 for blood removing are disposed on a blood removing target, the non-coated portion 32 and the distal portion 134 are disposed in the inferior vena cava that is a comparatively wide blood vessel, and the proximal portion 135 is disposed in the femoral vein that is a comparatively narrow blood vessel.

As illustrated in FIG. 9, a lock connector 136 has a first lock connector 137 which communicates with the first lumen 61, and a second lock connector 138 which is provided to be parallel to the first lock connector 137 and communicates with the second lumen 62. The lock connector 136 is a Y-connector having a Y-shape which is formed by the first lock connector 137 bifurcated from the second lock connector 138.

The first lock connector 137 is interlocked with the proximal portion of the inner tube 161. The second lock connector 138 is coaxially interlocked with the proximal portion of the proximal portion 135. A blood feeding tube (blood feeding line) is connected to the first lock connector 137, and a blood removing tube (blood removing line) is connected to the second lock connector 138.

The non-coated portion 32 and the distal portion 134 exhibit the same function as that in the first embodiment and also have an operational effect in common therewith.

As described above, according to the catheter 60 of the present embodiment, one catheter can perform both functions of blood removing and blood feeding.

Hereinabove, the catheter according to the present invention has been described through the embodiments. The present invention is not limited to only the configurations described in the embodiments and the modification example and can be suitably changed based on Claims.

For example, in the first embodiment described above, when a material having hardness higher than that of the resin material 331a provided in the distal portion 331 is used as the resin material 332a provided in the proximal portion 332, the proximal portion 332 is configured to have flexibility lower than that of the distal portion 331. However, in place thereof or in addition thereto, the flexibility of the proximal portion 332 may be decreased compared to the distal portion 331 by constituting the wires W in the proximal portion 332 to be braided in a denser manner than the wires W in the distal portion 331. Moreover, the flexibility of the proximal portion 332 may be decreased compared to the distal portion 331 by further increasing the wire diameter of the wires W in the proximal portion 332 compared to the wire diameter of the wires W in the distal portion 331.

In addition, a material constituting the wires W is not limited to a shape memory material as long as the material has a restoring force for being deformed and returning to the original shape and has a function of reinforcing the resin layer. For example, the wires W can be formed of a known elastic material.

In addition, in the second embodiment described above, the non-coated portion 32 and the side hole 164 for blood removing are used for blood removing, and the side hole 163 for blood feeding is used for blood feeding. However, the non-coated portion 32 and the side hole 164 are used for blood feeding, and the side hole 163 is used for blood removing.

In addition, in the first embodiment described above, the coated portion 33 has the distal portion 331 and the proximal portion 332 which has flexibility lower than that of the distal portion 331. However, the coated portion 33 may be configured to have uniform flexibility.

In addition, in the first embodiment described above, the distal end 32a of the non-coated portion 32 is formed to have a tapered shape reduced in diameter toward the distal side, and the distal tip 41 internally holds the distal end 32a of the non-coated portion 32. However, the configuration is not particularly limited as long as the distal tip 41 is fixed to the distal end 32a of the non-coated portion 32.

What is claimed is:

1. A percutaneous catheter through which blood passes and which expands in an axial direction in response to a dilator being fully inserted through the percutaneous catheter, comprising:
    a catheter tube that extends in an axial direction and is comprised of wires braided in an intersecting manner; and
    a distal tip affixed on a distal side of the catheter tube and configured to conform to a distal end of the dilator that engages the distal tip;
    wherein the catheter tube includes:
        a non-coated portion which is provided on a proximal side of the distal tip; and
        a coated portion which is provided on the proximal side of the non-coated portion and is formed by coating the braided wires with a resin material;
    wherein a nominal inner diameter of the non-coated portion is configured to be larger than an outer diameter of the dilator before the dilator is inserted through the percutaneous catheter;
    wherein when the dilator is fully inserted through the percutaneous catheter, the non-coated portion expands in the axial direction and is reduced in inner diameter so that an inner peripheral portion of the non-coated portion comes into tight contact with an outer peripheral portion of the dilator;
    wherein the coated portion has a distal coated portion which is provided on the distal side, and a proximal coated portion which is provided on the proximal side of the distal coated portion, and wherein the proximal coated portion has flexibility lower than flexibility of the distal coated portion;
    wherein an inner diameter of the distal coated portion is configured to be larger than the outer diameter of the dilator before the dilator is inserted through the percutaneous catheter, and wherein when the dilator is fully inserted through the percutaneous catheter, the distal coated portion expands in the axial direction and is reduced in inner diameter so that an inner peripheral portion of the distal coated portion comes into tight contact with the outer peripheral portion of the dilator; and
    wherein the distal coated portion and the non-coated portion of the catheter tube are configured to indwell in a living body with expanded diameters after the dilator is withdrawn from the percutaneous catheter.

2. The percutaneous catheter according to claim 1:
    wherein a distal end of the non-coated portion is formed to have a tapered shape reduced in diameter toward the distal side;
    wherein the distal tip internally holds the distal end of the non-coated portion; and
    wherein the distal tip is formed of a hard plastic which prevents the distal end of the non-coated portion from being squashed.

3. The percutaneous catheter according to claim 1 wherein the wires are formed of a shape memory material.

4. A percutaneous catheter assembly comprising:
    a dilator;
    a catheter tube that extends in an axial direction and is comprised of wires braided in an intersecting manner; and
    a distal tip affixed on a distal side of the catheter tube and configured to conform to a distal end of the dilator that engages the distal tip;
    wherein the catheter tube includes:
        a non-coated portion which is provided on a proximal side of the distal tip; and
        a coated portion which is provided on the proximal side of the non-coated portion and is formed by coating the braided wires with a resin material;
    wherein a nominal inner diameter of the non-coated portion is configured to be larger than an outer diameter of the dilator before the dilator is inserted through the percutaneous catheter;
    wherein when the dilator is fully inserted through the percutaneous catheter, the non-coated portion expands in the axial direction and is reduced in inner diameter so that an inner peripheral portion of the non-coated portion comes into tight contact with an outer peripheral portion of the dilator;
    wherein the coated portion has a distal coated portion which is provided on the distal side, and a proximal coated portion which is provided on the proximal side of the distal coated portion, and wherein the proximal portion has flexibility lower than flexibility of the distal portion;
    wherein an inner diameter of the distal coated portion is configured to be larger than the outer diameter of the dilator before the dilator is inserted through the percutaneous catheter; and wherein when the dilator is fully inserted through the percutaneous catheter, the distal coated portion expands in the axial direction and is reduced in inner diameter so that an inner peripheral portion of the distal coated portion comes into tight contact with the outer peripheral portion of the dilator; and
    wherein the distal coated portion and the non-coated portion of the catheter tube are configured to indwell in a living body with expanded diameters after the dilator is withdrawn from the percutaneous catheter.

5. The percutaneous catheter assembly according to claim 4:
wherein a distal end of the non-coated portion is formed to have a tapered shape reduced in diameter toward the distal side;
wherein the distal tip internally holds the distal end of the non-coated portion; and
wherein the distal tip is formed of a hard plastic which prevents the distal end of the non-coated portion from being squashed.

6. The percutaneous catheter assembly according to claim 4 wherein the wires are formed of a shape memory material.

7. A percutaneous catheter through which blood passes and which expands in an axial direction in response to a dilator being fully inserted through the percutaneous catheter, comprising:
a catheter tube that extends in an axial direction and is comprised of wires braided in an intersecting manner; and
a distal tip affixed on a distal side of the catheter tube and configured to conform to a distal end of the dilator that engages the distal tip;
wherein the catheter tube includes:
a non-coated portion which is provided on a proximal side of the distal tip; and
a coated portion which is provided on the proximal side of the non-coated portion and is formed by coating the braided wires with a resin material;
wherein a nominal inner diameter of the non-coated portion is configured to be larger than an outer diameter of the coated portion before the dilator is inserted through the percutaneous catheter;
wherein when the dilator is fully inserted through the percutaneous catheter, the non-coated portion and the coated portion expand in the axial direction, whereby the non-coated portion is reduced in inner diameter so that an inner peripheral portion of the non-coated portion comes into tight contact with an outer peripheral portion of the dilator
wherein the coated portion has a distal coated portion which is provided on the distal side, and a proximal coated portion which is provided on the proximal side of the distal coated portion, and wherein the proximal coated portion has flexibility lower than flexibility of the distal coated portion;
wherein an inner diameter of the distal coated portion is configured to be larger than the outer diameter of the dilator before the dilator is inserted through the percutaneous catheter, and wherein when the dilator is fully inserted through the percutaneous catheter, the distal coated portion expands in the axial direction and is reduced in inner diameter so that an inner peripheral portion of the distal coated portion comes into tight contact with the outer peripheral portion of the dilator; and
wherein the distal coated portion and the non-coated portion of the catheter tube are configured to indwell in a living body with expanded diameters after the dilator is withdrawn from the percutaneous catheter.

8. The percutaneous catheter according to claim 7:
wherein a distal end of the non-coated portion is formed to have a tapered shape reduced in diameter toward the distal side;
wherein the distal tip internally holds the distal end of the non-coated portion; and
wherein the distal tip is formed of a hard plastic which prevents the distal end of the non-coated portion from being squashed.

9. The percutaneous catheter according to claim 7 wherein the wires are formed of a shape memory material.

* * * * *